United States Patent [19]

Bormann

[11] Patent Number: 4,530,842

[45] Date of Patent: Jul. 23, 1985

[54] 2(1H)-PYRIDINONE DERIVATIVES, THEIR PREPARATION AND PHARMACEUTICAL COMPOSITIONS CONTAINING THEM

[75] Inventor: Gerhard Bormann, Münchenstein, Switzerland

[73] Assignee: Sandoz Ltd., Basel, Switzerland

[21] Appl. No.: 493,933

[22] Filed: May 12, 1983

[30] Foreign Application Priority Data

| May 18, 1982 | [CH] | Switzerland | 3087/82 |
| May 18, 1982 | [CH] | Switzerland | 3091/82 |
| Feb. 15, 1983 | [CH] | Switzerland | 837/83 |

[51] Int. Cl.³ .................. C07D 213/57; A61K 31/44
[52] U.S. Cl. .................................. 514/344; 546/288; 546/292; 546/297
[58] Field of Search .................. 546/288; 424/263

[56] References Cited

U.S. PATENT DOCUMENTS

| 3,814,771 | 6/1974 | Shen et al. | 546/193 |
| 4,209,626 | 1/1980 | Trust et al. | 546/119 |
| 4,244,953 | 1/1981 | Trust et al. | 424/256 |

FOREIGN PATENT DOCUMENTS

| 61774 | 10/1982 | European Pat. Off. | 546/261 |
| 74091 | 3/1983 | European Pat. Off. | 546/298 |
| 1271767 | 4/1972 | United Kingdom | 546/298 |

Primary Examiner—Alan L. Rotman
Attorney, Agent, or Firm—Gerald D. Sharkin; Robert S. Honor

[57] ABSTRACT

The compounds of formula I

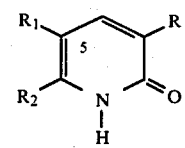

wherein R, $R_1$ and $R_2$ have various significances, are useful as agents against heart insufficiency.

4 Claims, No Drawings

2(1H)-PYRIDINONE DERIVATIVES, THEIR PREPARATION AND PHARMACEUTICAL COMPOSITIONS CONTAINING THEM

The present invention relates to 2(1H)-pyridinone derivatives, their preparation and pharmaceutical compositions containing them.

In particular the invention provides compounds of formula I

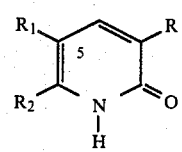

wherein
R is cyano, carbamoyl or amino and either
(a) $R_1$ is
(i) phenyl mono- or independently disubstituted by a group $-(CH_2)_mX$ or $-(CH_2)_nY$ wherein
m is a whole number from 0 to 4,
n is a whole number from 1 to 4,
X is cyano, carboxy, alkoxycarbonyl of 2 to 5 carbon atoms in the aggregate thereof, carbamoyl or alkylsulfinyl of 1 to 4 carbon atoms and
Y is hydroxy, alkoxy of 1 to 4 carbon atoms, halogen of atomic number of from 9 to 35 or amino or
(ii) phenyl disubstituted by a group $-(CH_2)_mX$ or $-(CH_2)_nY$ wherein m, n, X and Y are defined above and by alkyl of 1 to 4 carbon atoms, alkoxy of 1 to 4 carbon atoms or halogen of atomic number of from 9 to 35 and
$R_2$ is hydrogen or alkyl of 1 to 4 carbon atoms or
(b) $R_1$ is hydrogen or alkyl of 1 to 4 carbon atoms or has the significance indicated under (a) above for $R_1$ and
$R_2$ has the significance indicated under (a) above for $R_1$,
hereinafter referred to as "the compounds of the invention".

It is to be appreciated that for the sake of simplicity the compounds of the invention are defined with reference to the tautomeric form of Formula I. However, the invention extends to all tautomeric forms of the compounds, e.g., the iminolform.

R preferably is cyano or amino, especially cyano. $R_1$ preferably is as defined under (a) above. When it is as defined under (a) above it preferably has significance (i). When it is as defined above (b) above it preferably is hydrogen or alkyl, especially alkyl. $R_2$ preferably is as defined under (a) above. When it is as defined under (a) above it preferably is alkyl. When it is as defined under (b) above it preferably has significance (i).

A phenyl ring preferably is monosubstituted. When it is monosubstituted the substituent preferably is in the para position. When it is disubstituted the substituents preferably are in the meta and para positions. When it is disubstituted and/or or when both $R_1$ and $R_2$ have the significance indicated under (a) above for $R_1$ the phenyl ring substituents preferably are identical.

Significance (i) is preferred over significance (ii). Significance (i) preferably is phenyl mono- or independently disubstituted by a group $-(CH_2)_mX$. Significance (ii) preferably is phenyl independently disubstituted by a group $-(CH_2)_mX$ and by alkyl, alkoxy or halogen.

m preferably is 0, 1 or 2, especially 0 or 1, especially 0. n preferably is 1 or 2, especially 1. X preferably is cyano or carboxy, especially cyano. Y preferably is hydroxy or amino, especially hydroxy.

Alkyl, alkoxy, the alkoxy part of alkoxycarbonyl and/or alkylsulfinyl preferably are of 1 or 2, especially of 1 carbon atom. Halogen preferably is chlorine or bromine, especially chlorine.

A preferred group of compounds of the invention is the compounds of formula Ia,

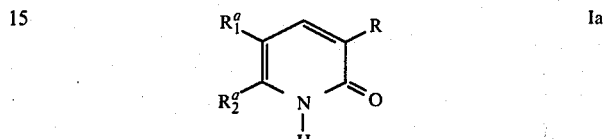

wherein R is as defined above and $R_1^a$ and $R_2^a$ have the significance indicated under (a) above for $R_1$ and $R_2$. In a subgroup all phenyl ring substituents when other than hydrogen are identical.

A preferred subgroup of compounds of formula Ia is the compounds of formula Iaa,

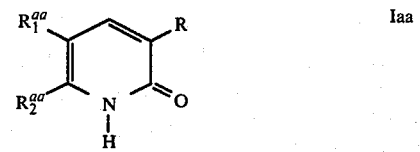

wherein
R is as defined above,
$R_1^{aa}$ has significance (i) indicated above for $R_1$ and
$R_2^{aa}$ is alkyl of 1 to 4 carbon atoms.

In a subgroup of compounds of formula Iaa R is cyano. In another subgroup R is amino. In another subgroup all phenyl ring substituents when other than hydrogen are identical.

A preferred subgroup of compounds of formula Iaa is the compounds of formula Iaaa,

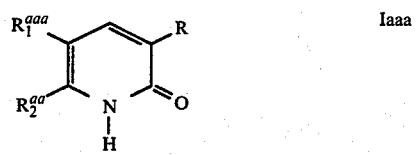

wherein
R and $R_2^{aa}$ are as defined above and
$R_1^{aaa}$ is phenyl mono- or independently disubstituted by a group $-(CH_2)_{m'}X^a$ or $-(CH_2)_{n'}Y^a$ wherein
m' is a whole number from 0 to 2,
n' is the whole number 1 or 2,
$X^a$ is cyano or carboxy and
$Y^a$ is hydroxy or amino.

In a subgroup of compounds of formula Iaaa $R_1^{aaa}$ is phenyl monosubstituted by a group $-(CH_2)_{m'}X^a$ or $-(CH_2)_{n'}Y^a$ as defined above. In another subgroup R is cyano. In another subgroup R is amino. In a further subgroup m' is 0 and n' is 1. In a further subgroup $X^a$ is cyano. In a further subgroup $Y^a$ is hydroxy. In a further subgroup all phenyl ring substituents when other than hydrogen are identical.

Another group of compounds of the invention is the compounds of formula Ib,

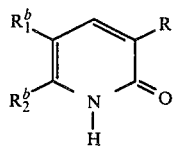

wherein R is as defined above and $R_1^b$ and $R_2^b$ have the significance indicated under (b) above for $R_1$ and $R_2$. In a subgroup all phenyl ring substituents when other than hydrogen are identical.

A further preferred group of compounds of the invention is the compounds of formula Ic,

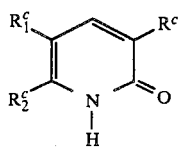

wherein $R^c$, $R_1^c$ and $R_2^c$ have the significance indicated above for R, $R_1$ and $R_2$ with the proviso that, when $R^c$ is amino, then X is cyano and Y is hydroxy or alkoxy of 1 to 4 carbon atoms.

In a subgroup of compounds of formula Ic $R^c$ is cyano or carbamoyl.

Another group of compounds of the invention is the compounds of formula Ipa,

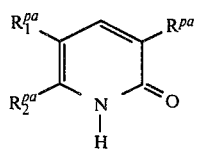

wherein $R^{pa}$ is cyano or carbamoyl and either (a) $R_1^{pa}$ is (i) phenyl mono- or independently disubstituted by alkylsulfinyl of 1 to 4 carbon atoms, (ii) phenyl disubstituted by a group alkylsulfinyl of 1 to 4 carbon atoms and by alkyl of 1 to 4 carbon atoms, alkoxy of 1 to 4 carbon atoms or halogen or atomic number of from 9 to 35 or (iii) phenyl monosubstituted by cyano or carboxy and $R_2^{pa}$ is hydrogen or alkyl of 1 to 4 carbon atoms or (b) $R_1^{pa}$ is hydrogen or alkyl of 1 to 4 carbon atoms or has the significance indicated under (a) above for $R_1^{pa}$ and $R_2^{pa}$ has the significance indicated under (a) above for $R_1^{pa}$.

Another group of compounds of the invention is the compounds of formula Ipb,

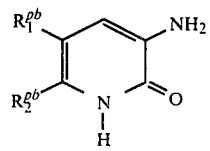

wherein $R_1^{pb}$ and $R_2^{pb}$ have the significance indicated above for $R_1^{pa}$ and $R_2^{pa}$.

Another group of compounds of the invention is the compounds of formula Ipc,

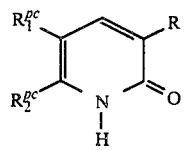

wherein

R is as defined above and either (a) $R_1^{pc}$ is phenyl monosubstituted by a group —$(CH_2)_{mp}X^p$ or —$(CH_2)_nY^p$ wherein mp is a whole number from 1 to 4, n is as defined above, $X^p$ is carboxy or alkoxycarbonyl of 2 to 5 carbon atoms in the aggregate thereof and $Y^p$ is hydroxy or alkoxy of 1 to 4 carbon atoms and $R_2^{pc}$ is hydrogen or alkyl of 1 to 4 carbon atoms, or (b) $R_1^{pc}$ is hydrogen or alkyl of 1 to 4 carbon atoms or has the significance indicated under (a) above for $R_1^{pc}$ and $R_2^{pc}$ has the significance indicated under (a) above for $R_1^{pc}$, whereby the substituents on the two phenyl rings are identical.

Another group of compounds of the invention is the compounds of formula Is

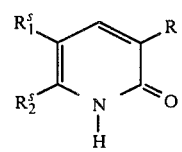

wherein

R is as defined above, $R_1^s$ is (i) phenyl monosubstituted by a group —$(CH_2)_{ms}X^s$ or —$(CH_2)_{ns}OH$ wherein ms is a whole number from 0 to 2, ns is the whole number 1 or 2 and $X^s$ is cyano, carboxy or carbamoyl or (ii) phenyl disubstituted by alkylsulfinyl of 1 or 2 carbon atoms and by alkoxy of 1 to 4 carbon atoms and $R_2^s$ is alkyl of 1 or 2 carbon atoms.

A compound of the invention may be obtained by a process comprising (a) for the production of a compound of formula I'

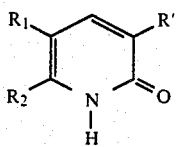

I' wherein $R_1$ and $R_2$ are as defined above and R' is cyano or carbamoyl, reacting a corresponding compound of formula II

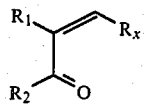

II wherein $R_1$ and $R_2$ are as defined above and $R_x$ is a leaving group, with a corresponding compound of formula III

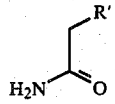

III wherein R' is as defined above or (b) for the production of a compound of formula I''

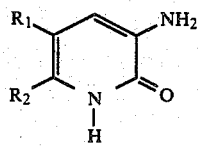

I'' wherein $R_1$ and $R_2$ are as defined above, aminating a corresponding compound of formula IV

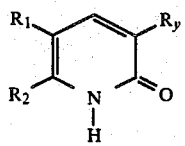

IV wherein $R_1$ and $R_2$ are as defined above and $R_y$ is a group capable of conversion to a primary amino group.

Process variant (a) may be effected in conventional manner for the production of analogous 3-cyano- or 3-carbamoyl-2(1H)-pyridinone derivatives. $R_x$ may be a conventional radical such as di(lower)alkylamino, especially dimethylamino or diethylamino, used for cyclization with an acetamide compound. The reaction preferably is effected in an inert solvent such as ethanol. Suitable reaction temperatures may be from room temperature to about the boiling temperature of the reaction mixture. Preferably strongly alkaline conditions are used.

The reaction may however also be effected in an acidic medium, e.g. in the presence of acetic acid. In this situation a compound of formula I' wherein R' is carbamoyl may be obtained directly when starting from a corresponding compound of formula III wherein R' is cyano.

It may be indicated to effect the cyclization with a phenyl ring substituent such as cyano-methyl in a precursor form such as bromomethyl and to convert the precursor substituent into the desired substituent after cyclization has been effected, e.g. bromomethyl to cyanomethyl.

Process variant (b) may be effected in conventional manner for the production of analogous 3-amino-2(1H)-pyridinone derivatives. $R_y$ may be a conventional radical used for conversion to a primary amino group, such as nitro and especially carbamoyl. For example, when $R_y$ is carbamoyl, the reaction conditions of a Hofmann degradation may be used. The reaction preferably is effected under strongly alkaline conditions, e.g. in the presence of an alkali metal hydroxide and bromine. Preferably water is used as a solvent. Suitable reaction temperatures may be from about 50° to about 100° C., conveniently about 100° C.

It may be indicated to effect the amination with a phenyl ring substituent such as carbamoyl or cyano in a precursor form such as cyano or bromine, respectively, and to convert the precursor substituent into the desired substituent after amination has been effected, e.g. cyano to carbamoyl, or bromine to cyano.

A compound of the invention may be isolated from the reaction mixture and purified in a manner analogous to known methods.

A compound of the invention may exist in free form or in salt form. A free form may be converted into a salt form in conventional manner and vice-versa. Suitable acids for acid addition salt formation include hydrochloric, malonic, p-toluene sulfonic and methanesulfonic acid. Suitable bases for anionic salt formation include sodium and potassium hydroxide. A compound in anionic salt form possesses in general predominantly the iminol form.

A starting material may be obtained in known manner.

A compound of formula II wherein $R_x$ is di(lower)alkylamino may e.g. be obtained by reacting a corresponding compound of formula V

V wherein $R_1$ and $R_2$ are as defined above, with an N,N-di(lower)alkyl formamide di(lower)alkyl acetal, preferably N,N-dimethylformamide dimethyl or diethyl acetal.

A compound of formula V may be obtained in accordance with known methods. For example, a compound of formula V wherein $R_1$ is phenyl mono- or identically disubstituted by a group $-(CH_2)_mX$ or $-(CH_2)_nY$ as defined above and $R_2$ is hydrogen or alkyl of 1 to 4 carbon atoms may be obtained according to the following scheme, whereby the reaction steps may be repeated for the production of compounds wherein m and/or n are a number up to 4 and whereby the carbonyl group preferably is reacted in protected form, e.g. as ketal:

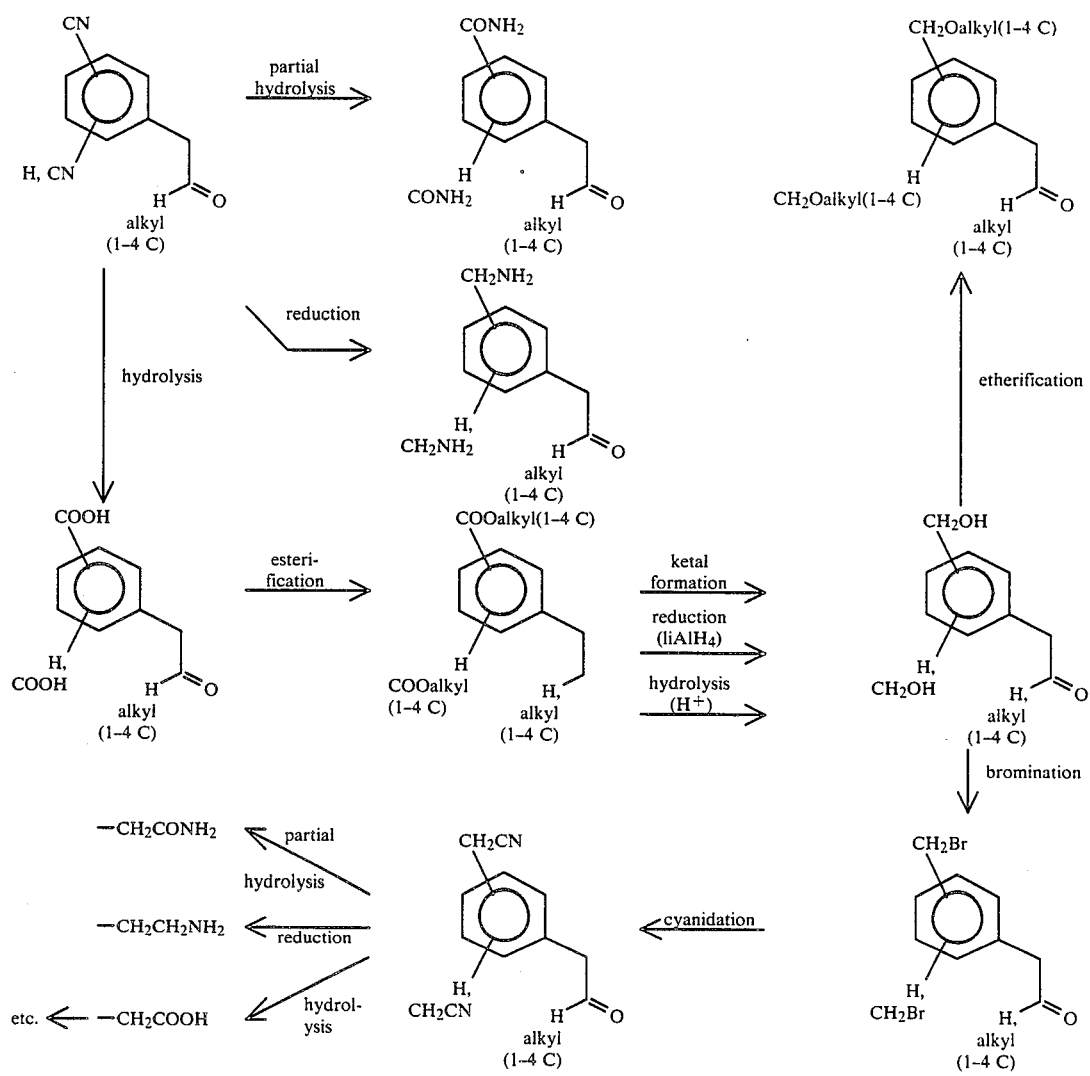

Further compounds of formula V may be obtained in analogous manner. An alkylsulfinyl substituent may be obtained by oxydation of an alkylthio substituent, e.g with hydrogen peroxide or m-chloroperbenzoic acid.

Insofar as the preparation of any particular starting material is not particularly described, this may be effected in conventional manner or in analogous manner to that described herein.

In the following Examples all temperatures are in degrees Centigrade and are uncorrected.

EXAMPLE 1

5-(4-cyanophenyl)-1,2-dihydro-6-methyl-2-oxopyridine-3-carbonitrile (process variant a)

6.2 g of cyanacetamide are added to a freshly prepared solution of 1.14 g sodium in 200 ml of absolute ethanol. 10.6 g 4-dimethylamino-3-(4-cyanophenyl)-3-buten-2-one are added and the solution is stirred 5 hours at boiling temperature, whereby the sodium salt of the title compound soon begins to crystallize out. The mixture is allowed to cool, the crystalline product is filtered and washed with ethanol and ether (m.p. of the sodium salt > 300°) (m.p. of the free form > 300°).

The starting material 4-dimethylamino-3-(4-cyanophenyl)-3-buten-2-one (b.p. 0.005 mm Hg = 155°-160°) is obtained by heating 1-(4-cyanophenyl)-2-propanone with N,N-dimethylformamide dimethyl acetal at 80° for 1 hour.

EXAMPLE 2

4-(3-cyano-1,2-dihydro-6-methyl-2-oxopyridin-5-yl)-phenyl acetic acid (process variant a)

11 g 4-dimethylamino-3-(4-methoxycarbonylmethylphenyl)-3-buten-2-one are reacted with cyanacetamide as described in Example 1. The title compound is obtained (m.p. 280°-282°—from dimethylformamide/ethanol).

The starting material is obtained as follows:

4-(2-Oxopropyl)benzonitrile is heated to boiling temperature for 5 hours in concentrated aqueous hydrochloric acid solution. The resultant 4-(2-oxopropyl)benzoic acid (m.p. 163°-165°) is reacted with hydrochloric acid gas in methanol. The carbonyl group in the resultant methyl-4-(2-oxopropyl)benzoate (m.p. 48°-50°) is protected as ketal by reaction with ethylene glycol in the presence of p-toluene sulfonic acid and the ketal reacted with lithium aluminium hydride in tetrahydrofuran. The protecting group in the resultant 2-(4-hydroxymethylbenzyl)-2-methyl-1,3-dioxolane (b.p. 0.07 mm Hg = 130°-135°) is removed with 2N aqueous hydrochloric acid solution and the resultant deprotected compound is brominated in ether with phosphorus tribromide. The resultant 1-(4-bromomethylphenyl)-2-propanone is reacted without further characterization with an excess of sodium cyanide in ethanol and the resultant 4-(2-oxopropyl)phenyl acetonitrile (b.p. 0.1 mm Hg=140°) is hydrolyzed with concentrated aqueous hydrochloric acid solution. The resultant 4-(2-oxopropyl)phenyl acetic acid, (m.p. 92°-94°) is esterified with methanol. The resultant methyl-4-(2-oxopropyl)phenylacetate (b.p. 0.06 mm Hg=120°-130°) is reacted for 2 hours at 50° with N,N-dimethylformamide dimethyl acetal. The resultant 4-dimethylamino-3-(4-methoxycarbonylmethylphenyl)-3-buten-2-one is reacted further in crude form.

EXAMPLE 3

3-amino-5-(2-methoxy-4-methylsulfinylphenyl)-6-methyl-2(1H)-pyridinone (process variant b)

3.7 ml of bromine are added dropwise to a stirred solution of 15 g sodium hydroxide in 230 ml water at 0°. 17.6 g 1,2-dihydro-5-(2-methoxy-4-methylthiophenyl)-6-methyl-2-oxonicotinamide are then added and the mixture is heated at 100° for 3 hours. The mixture is allowed to cool to room temperature and then carefully acidified with 6N hydrochloric acid, agitated for a further 30 minutes and the brown precipitate is then filtered off. The filtrate is extracted with ethyl acetate and the aqueous phase concentrated and made alkaline with ammonium hydroxide. The precipitate is filtered off and the supernatant concentrated. The title compound crystallizes out (m.p. of the hydrochloride form 224°-226°—from methylene chloride/methanol).

The starting material 1,2-dihydro-5-(2-methoxy-4-methylthiophenyl)-6-methyl-2-oxonicotinamide (m.p. 278°-281° [dec.]—from methylene chloride/methanol) is obtained by heating to ebullition 2-methoxy-4-methylthiobenzaldehyde with nitroethane in toluene in the presence of n-butylamine, converting the resultant nitrovinyl compound with iron powder and hydrochloric acid without further characterization to 1-(2-methoxy-4-methylthiophenyl)-2-propanone (b.p. 0.02 mm Hg=140°-150°), heating this compound with N,N-dimethylformamide dimethyl acetal for 3 hours to 80° and reacting the resultant 4-dimethylamino-3-(2-methoxy-4-methylthiophenyl)-3-buten-2-one (m.p. 111°-112°—from ether/petroleum ether) with cyanacetamide in glacial acetic acid at 100°.

The following compounds of the invention may be obtained in analogous manner:

| Example No. | R | $R_1$ | $R_2$ | m.p. |
|---|---|---|---|---|
| (a) Analogous to Examples 1 and 2: | | | | |
| 4 | $CONH_2$ | 4-CN—Phe | Me | b>300° |
| 5 | CN | 2-MeO—4-MeSO—Phe | Me | k>300° |
| 6 | CN | 4-COOH—Phe | Me | b>300° |
| 7 | CN | 4-CH$_2$OH—Phe | Me | na>300° |
| (b) Analogous to Example 3: | | | | |
| 8 | $NH_2$ | 4-COOH—Phe | Me | b 290-293° |

Me = methyl
Phe = phenyl
m.p. = melting point
b = in free form
k = in potassium salt form
na = in sodium salt form The following compounds of the invention may also be obtained in analogous manner:

| Example | R | $R_1$ | $R_2$ |
|---|---|---|---|
| A | $CONH_2$ | 2-(2-aminoethyl)-5-isopropyl-Phe | Et |
| B | CN | 2-chloro-3-(2-fluoroethyl)-Phe | 2-Me—Pr |
| C | $CONH_2$ | 2-Br—4-(3-Cl—Pr)—Phe | H |
| D | $CONH_2$ | iPr | 3-CH$_2$CONH$_2$—5-(4-COOEt—Bu)—Phe |
| E | $NH_2$ | H | 3-(3-OH—Pr)—5-aminomethyl-Phe |
| F | CN | 3-Cl—5-COOiPr—Phe | 3-[(CH$_2$)$_4$—SO—tBu]Phe |

Bu = butyl
Et = ethyl
iPr = isopropyl
Phe = phenyl
Pr = propyl
tBu = tert-butyl

In a first group of compounds of the invention R is cyano.

In a second group of compounds of the invention R is carbamoyl.

In a third group of compounds of the invention R is amino.

In a fourth group of compounds of the invention $R_1$ and $R_2$ have significance (a).

In a fifth group of compounds of the invention $R_1$ is hydrogen or alkyl and $R_2$ has significance (b).

In a sixth group of compounds of the invention $R_1$ and $R_2$ both have the significance indicated under (a) for $R_1$.

In a seventh group of compounds of the invention $R_1$ has significance (i) and $R_2$ is hydrogen or alkyl.

In a eigth group of compounds of the invention $R_1$ has significance (ii) and $R_2$ is hydrogen or alkyl.

In a ninth group of compounds of the invention $R_2$ is hydrogen.

In a tenth group of compounds of the invention $R_2$ is akyl.

In a eleventh group of compounds of the invention significance (i) is phenyl monosubstituted by a group —(CH$_2$)$_m$X.

In a twelwth group of commands of the invention significance (i) is phenyl monosubstituted by a group —(CH$_2$)$_n$Y.

In a thirteenth group of compounds of the invention significance (i) is phenyl disubstituted by a group —(CH$_2$)$_m$X and/or —(CH$_2$)$_n$Y.

In a fourteenth group of compounds of the invention significance (i) is phenyl identically disubstituted by a group —(CH$_2$)$_m$X or —(CH$_2$)$_n$Y.

In a fifteenth group of compounds of the invention $R_2$ is methyl.

In a sixteenth group of compounds of the invention all phenyl ring substituents when other than hydrogen are identical.

In a seventeenth group of compounds of the invention m is 0.

In a eighteenth group of compounds of the invention m is 1.

In a nineteenth group of compounds of the invention n is 1.

In a twentieth group of compounds of the invention X is cyano.

In a twenty-first group of compounds of the invention X is alkylsulfinyl.

In a twenty-second group of compounds of the invention Y is hydroxy.

The compounds of the invention are useful because they possess pharmacological activity.

The compounds exhibit cardiotonic activity, as indicated by standard tests. For example, in the normotonic Numal anaesthetized dog, an increase in the contractile force of the left ventricle is observed upon intravenous administration of from about 0.02 mg/kg to about 2 mg/kg.

The test method is as follows:

Dogs of either sex weighing from 10 to 15 kg are used. Numal in a dosis of 65 mg/kg i.v. is used as an anaesthetic. The animal is attached in supine position on the operation table. After the usual preparations have been effected a heparinized catheter is introduced along the Arteria carotis dextra into the left ventricle under radiological control and the transmission of the pressure is registered with a donor membrane (Gould Statham P 23 Gb). The increase in pressure as a function of time is computed and registered with an HSE-physiodifferentiator. The pressure increase in the left ventricle is a measure of the contractile force of the heart. The magnitude of the pressure differential is indicated in mm Hg/sec. A suitable body temperature (about 36° to 37° C.) is maintained constant. After a control period of about 40 minutes the test substance is injected into the Vena femoralis and its effect on the registered or computed parameters observed.

The cardiotonic activity is accompanied by an afterload-reducing effect. Thus, in the above-mentioned anaesthetized dog test a reduction in arterial blood pressure and total peripheral resistance is observed after intravenous injection of from about 0.2 mg/kg to about 2 mg/kg.

For measurement of arterial blood pressure a heparinized catheter is introduced under radiological control over the Arteria femoralis sinistra into the base of the aorta. Arterial pressure is measured with a Statham pressure transducer P 23 AC, permitting a precise evaluation of systolic and diastolic pressure. The mean arterial pressure is computed by adding $\frac{1}{3}$ of the amplitude ($P_{systol.} - P_{diastol.}$) to the value for the diastolic pressure.

Total peripheral resistance (PR) is measured in dyn sec cm$^{-5}$ according to the formula:

$$PR = \frac{\text{mean arterial blood pressure} - \text{left ventricular diastolic pressure}}{\text{cardiac output}} \times 80$$

whereby the cardiac output determination is effected according to the thermodilution method using a catheter introduced under radiological control into the Vena jugularis dextra.

Further, the compounds of the invention as indicated by the Example 1 compound have an unexpectedly long duration of action and are unexpectedly well-tolerated. For example, there is surprisingly little associated tachycardia.

The compounds are therefore particularly useful as cardiotonic agents, e.g. for the treatment of heart insufficiency.

Preferred are the compounds of Example 1, 2 and 5, especially the compound of Example 1.

For the above-mentioned cardiotonic use the dosage will, of course, vary depending on the compound employed, mode of administration and treatment desired. However, in general, satisfactory results are obtained when administered at a daily dosage of from about 0.1 mg to about 10 mg per kg animal body weight, conveniently given in divided doses 2 to 4 times a day or in sustained release form. For the larger mammals the total daily dosage is in the range of from about 10 mg to about 500 mg and dosage forms suitable for oral administration comprise from about 2.5 mg to about 250 mg of the compounds admixed with a solid or liquid pharmaceutical carrier or diluent. An example of a daily dosage is from 10 mg to 100 mg.

The compounds may be administered in similar manner to known standards, for example digoxine. The suitable daily dosage for a particular compound will depend on a number of factors such as its relative potency of activity. It has for example been determined that the title compound of Example 1 in the above-mentioned Numal anaesthetized dog test has the following activity profile compared with digoxine:

| Compound | Dosage (mg/kg i.v.) | Increase in contractile force (%) |
|---|---|---|
| Example 1 | 0.002 to 0.2 | 22 to 184 |
| Digoxine | 0.02 to 0.08 | 5 to 45 |

It is therefore indicated that the compounds may be administered at similar or lower dosages than conventionally employed for digoxine.

The compounds may be administered in free form or in pharmaceutically acceptable salt form. Such salt forms exhibit the same order of activity as the free forms and are readily prepared in conventional manner. The present invention also provides a pharmaceutical composition comprising a compound of the invention in free form or in pharmaceutically acceptable salt form, in association with a pharmaceutical carrier or diluent. Such compositions may be in the form of, for example, a solution or a tablet. Solubilizing or stabilizing agents such as cyclodextrines, e.g., β-cyclodextrine, may appropriately be used for making a a solution.

I claim:

1. A compound of formula I

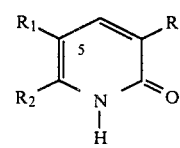

wherein
R is cyano,
R$_1$ is phenyl mono- or independently disubstituted by cyano, and
R$_2$ is hydrogen or alkyl of 1–4 carbon atoms,
in free form or in pharmaceutically acceptable salt form.

2. The compound of claim 1 which is 5-(4-cyanophenyl)-1,2-dihydro-6-methyl-2-oxopyridine-3-carbonitrile in free form or in pharmaceutically acceptable salt form.

3. A pharmaceutical composition comprising a compound of claim 1 in free form or in pharmaceutically acceptable salt form in association with a pharmaceutical carrier or diluent.

4. A method of treating heat insufficiency which comprises administering to an animal in need of such treatment a therapeutically effective amount of a compound of claim 1 in free form or in pharmaceutically acceptable salt form.

* * * * *